(12) United States Patent
Strick et al.

(10) Patent No.: US 7,052,650 B2
(45) Date of Patent: May 30, 2006

(54) APPARATUS AND METHOD FOR THE MANIPULATION AND TESTING OF MOLECULES, AND IN PARTICULAR OF DNA

(75) Inventors: Terrence R. Strick, Paris (FR); Jean F. Allemand, Arcueil (FR); David Bensimon, Paris (FR); Aaron Bensimon, Antony (FR); Vincent Croquette, Antony (FR)

(73) Assignee: Center National de la Recherche Scientifique (CNRS), Paris (FR)

( * ) Notice: Subject to any disclaimer, the term of this patent is extended or adjusted under 35 U.S.C. 154(b) by 210 days.

(21) Appl. No.: 10/163,089

(22) Filed: Jun. 6, 2002

(65) Prior Publication Data
US 2003/0027187 A1    Feb. 6, 2003

Related U.S. Application Data

(63) Continuation of application No. 09/049,200, filed on Mar. 27, 1998, now abandoned.
(60) Provisional application No. 60/041,744, filed on Mar. 28, 1997.

(51) Int. Cl.
*G01N 21/00* (2006.01)
(52) U.S. Cl. .................. 422/50; 422/55; 422/57; 436/501; 436/524; 436/527; 436/533; 435/7.21; 435/7.5; 435/7.6; 435/7.9; 536/23.1; 356/302; 356/305; 356/330; 356/904; 356/929; 356/958; 251/414; 251/421; 251/422; 251/427
(58) Field of Classification Search ............. 422/50, 422/55, 51, 58, 62, 99, 186.01; 436/501, 436/524, 527, 533; 435/7.21, 7.5, 7.6, 7.9; 536/23.1; 356/302, 305, 330, 904, 929, 958; 209/213, 217; 251/414, 421, 422, 427
See application file for complete search history.

(56) References Cited

U.S. PATENT DOCUMENTS 3,860,344 A  *  1/1975  Garfunkel ............... 356/51

(Continued)

OTHER PUBLICATIONS

P. Cluzel, et al., "DNA: An Extensible Molecule", *Science*, 271, No. 5250, (1996), pp. 792-794.

(Continued)

*Primary Examiner*—Long V. Le
*Assistant Examiner*—Pensee T. Do
(74) *Attorney, Agent, or Firm*—Finnegan, Henderson, Farabow, Garrett & Dunner, L.L.P.

(57) ABSTRACT

Apparatus for the manipulating and testing of molecules and in particular of DNA comprising a surface on which the molecule is anchored on multiple points at one end and a paramagnetic bead on which said molecule is anchored on multiple points at its other end, magnetic means for applying a force to the bead, said magnetic means being used to control the stretching and rotation of said bead and molecule, optical magnification means and a camera for the visualisation of said bead, computer means to which the images of the camera are transmitted, said computer means comprising means for analyzing the motions of the bead. A method for the manipulating and testing of molecules and in particular of DNA in which a molecule is anchored at one end to a fixed surface and at its other end to a paramagnetic bead wherein said molecule is anchored on multiple points at each of said ends.

28 Claims, 9 Drawing Sheets

U.S. PATENT DOCUMENTS 5,486,457 A     1/1996   Butler et al.
5,532,132 A     7/1996   Wang et al.
5,976,896 A * 11/1999   Kumar et al. ............... 436/527

OTHER PUBLICATIONS

S.B. Smith, et al., "Overstretching B-DNA: The Elastic Response of Individual Double-Stranded and Single-Stranded DNA Molecules," *Science*, 271, No. 5250, (1996), pp. 795-799.

S.B. Smith, et al., "Direct Mechanical Measurements of the Elasticity of Single DNA Molecules by Using Magnetic Beads," *Science*, 258, No. 5085, (1992), pp. 1122-1126.

C. Bustamante, et al., "Entropic Elasticity of Λ-Phage DNA," *Science*, 265, No. 5178, (1994), pp. 1599-1600.

* cited by examiner

APPARATUS AND METHOD FOR THE MANIPULATION AND TESTING OF MOLECULES, AND IN PARTICULAR OF DNA

This application is a continuation of Ser. No. 09/049,200 filed on Mar. 27, 1998 now abandoned and claims benefit of 60/041,744 filed on Mar. 28,1997.

The present invention concerns an apparatus and a method for the manipulation and testing of molecules and in particular of DNA.

BACKGROUND OF THE INVENTION

The twisting and bending of DNA is an extensively studied aspect of its structure. It affects both structural transitions and interactions between DNA and other molecular complexes. For example, a locally underwound DNA is necessary for transcriptional activation and recombinational repair. Supercoiled DNA is also a key structural factor in chromosomal organization in which the winding of the molecule around histone proteins is necessary for DNA compaction. More specifically, the entropic tension generated in supercoiled DNA in anaphase during chromosomal condensation is released by the action of a specific enzyme, topoisomerase II, thus allowing the disentanglement and segregation of the chromosomes necessary before cell division.

In the last decade new tools (atomic-force-microscopy, optical tweezers, small glass fibers, . . . ) have been developed to manipulate small objects and also to investigate the forces involved in the systems studied.

[1] S. B. Smith, Y. Cui, C. Bustamante Science 271, 795 (1996)

[2] P. Cluzel, A. Lebrun, C. Heller, R. Lavery, J.-L. Viovy, D. Chatenay, F. Caron Science 271, 795 (1996).

Spectacular results were obtained on molecules such as DNA and various motor proteins: RNA polymerase, F1-ATP synthase and myosin, for example.

However, sophisticated instrumentation is required in most of these systems.

The glass fibers have the advantage of giving very quick results. However, they require one to calibrate their elasticity before any measurements are made and although they are able to measure forces stronger than Brownian ones, they are not sensitive enough to be used in the entropic regime (<1 pN).

The AFM may be used in the same way and has the same drawbacks.

Optical tweezers have also been used, for example to measure the force (~6 pN) produced by a single myosin on an actin filament (the two basic components of muscles). They also require a force calibration. One needs to know the relation between the intensity of the laser beam and the force applied to the system, and one has to determine it every time one changes the trapped object.

Further drawbacks of optical tweezers are the lack of total torsionnal control on DNA and the local heating of the solution by the focussed laser which increases the noise.

Another technique which has been proposed in

[3] Smith S. B., Finzi L., Bustamante C.—Science, vol. 258, Nov. 13, 1992, consists in chemically attaching the DNA molecules by one end to a glass surface and by the other end to a magnetic bead. The beads were manipulated by using magnetic and hydrodynamic forces and observed under an optical microscope. Extension versus force curves were obtained.

However, the apparatus and methods proposed in this article did not allow for twisting the molecules.

Also, sophisticated means were needed to infer the forces applied to the beads.

SUMMARY OF THE INVENTION

With the apparatus and method of the invention, one does not need force calibrations, nor sophisticated tools.

The apparatus simply comprises an optical microscope, magnets and a PC and the force measurements are reduced to position measurements.

The apparatus and method proposed by the invention have the advantage of permitting real time control of the twisting of a molecule such as DNA in a continuous, reversible and quantitative manner.

According to an aspect of the invention, the molecules are anchored at multiple points at one end to a motionless element and at the other end to a magnetic bead and magnets are provided to act on the bead. The multiple anchoring points permit the controlled twisting of the molecules, which was not possible with the method proposed in [3].

According to an other aspect, the invention proposes means to follow in real time the motion of the bead in the three spatial directions.

According to an other aspect of the invention, it is proposed to determine the value of the force applied to the bead by a computerized analysis of the Brownian motion of the bead. The Brownian motion is found to be a very simple way to measure forces at the molecular level, with a dynamic range of 5 decades and good reproducibility.

The present application also presents experimental tests, results and various applications.

In particular, with the method and apparatus described the stiffness of any microscopic damped oscillator can be measured, and, if it is attached to a surface with a flexible element, the force applied to it can also be obtained. The method is general and can be adapted to objects other than DNA, such as actin, myosin or tubulin fibers and rotary motors such as F1 ATP synthase.

For DNA studies, results are given for the elastic behavior of a torsionnally constrained single DNA molecule which demonstrate the ability to generate and detect very small changes in torsion.

The simplicity and the sensitivity of the apparatus and method proposed provide an interesting tool for force and topology studies at the molecular level.

DESCRIPTION OF THE PREFERED EMBODIMENTS

The Apparatus

Figure 1:
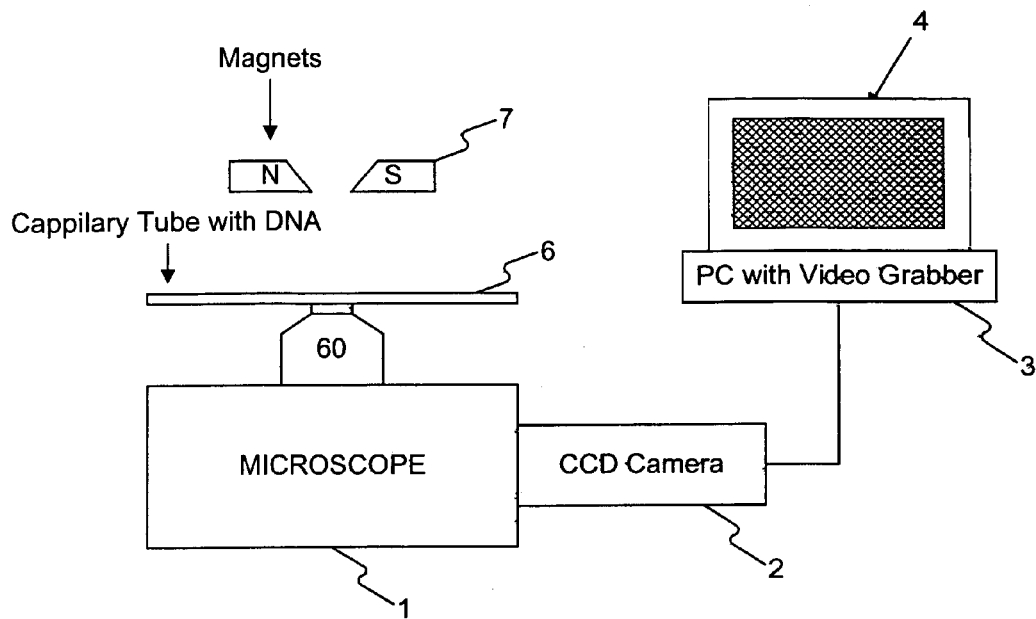
FIG. 1 and FIG. 2 are schematic drawings presenting the apparatus of the invention.
Figure 2:
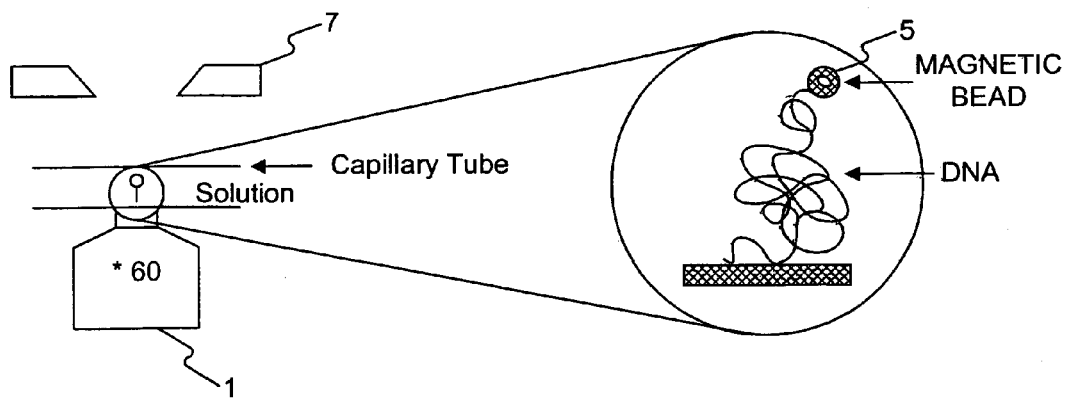

The apparatus which can be seen on FIGS. 1 and 2 comprises an inverted microscope (×60) 1 and a CCD camera 2 interposed between said microscope 1 and a video grabber 3 of a PC computer 4.

A molecule is attached by its extremities to a glass surface and to a superparamagnetic bead 5.

The glass surface is the internal surface of a capillary tube 6 which allows one to change the solutions where the DNA is immersed.

Permanent magnets 7 allow one to apply a force on the bead and consequently on the DNA molecule. By moving the magnets closer to or farther from the sample, one changes the magnetic field and thus controls the magnitude of the force applied to said beads 5.

Also, these magnets 7 can spin about the optical axis of the microscope 1, causing the paramagnetic beads 5 in the capillary tube 6 to rotate.

The beads 5 are for example latex beads with incorporated ferrites. They are super-paramagnetic and present a diameter of 2.8 or 4.5 μm. For the attacheament of DNA molecules multiply labelled with biotin and digoxigenin at their extremities, said beads are covered with streptavidin, whereas the capillary tube is coated with antidigoxigenin.

The microscope 1 is a Diaphot-200 Nikon with an immersion-oil objective. The X and Y axis are in the microscope focal plane and the Z-axis perpendicular to it.

Measurement of the xy Position and Fluctuations

In order to measure the xy fluctuations of a chosen bead, a target cross is placed on the image of the bead which is visualised on the screen of the computer 4.

The computer 4 memorises routines which enable it to follow the xy fluctuations of the center of the targeted bead.

In these routines, successive video frames are periodically sampled. For each frame, intensity profiles are averaged along the x and y directions. To determine the distance along x between the center of the cross and the center of the bead the intensity profile along x and its symmetric are used. With the maximum of the correlation product of the two profiles one measures twice the distance required. The same procedure is used in the y direction and thus the horizontal position of the bead is determined.

In the next video frame, the cross is placed at this position which is recorded. By iterating this procedure at each frame the bead is followed in real time in the xy plane. Practically that means that the cross is exactly follows She bead one image later. These fluctuations will be used to measure the force and the length. The precision reached is about 1 nm.

Measurement of the z Position and Fluctuations

The measurement of the z fluctuations uses the image of the diffraction pattern of the bead which varies with its position relative to the focal plane. The idea is to compare in real time the image of the bead to a reference set of images.

The reference set of images is built at high force when the molecule is fully extended and so rigid that the bead is quite immobile. The objective is then moved by known steps. The displacements of the objective are measured with a laser (fixed on the objective) illuminating a two quadrant detector. Rather than directly comparing full images (which would take too much time and memory) it is better to compare intensity profiles obtained by averaging the light levels over circles centered on the bead. One can measure relative displacements of about 1 nm.

The reference set of profiles is to be determined for each bead before any measurement whereas the procedure for the xy fluctuations is general.

Figure 3:
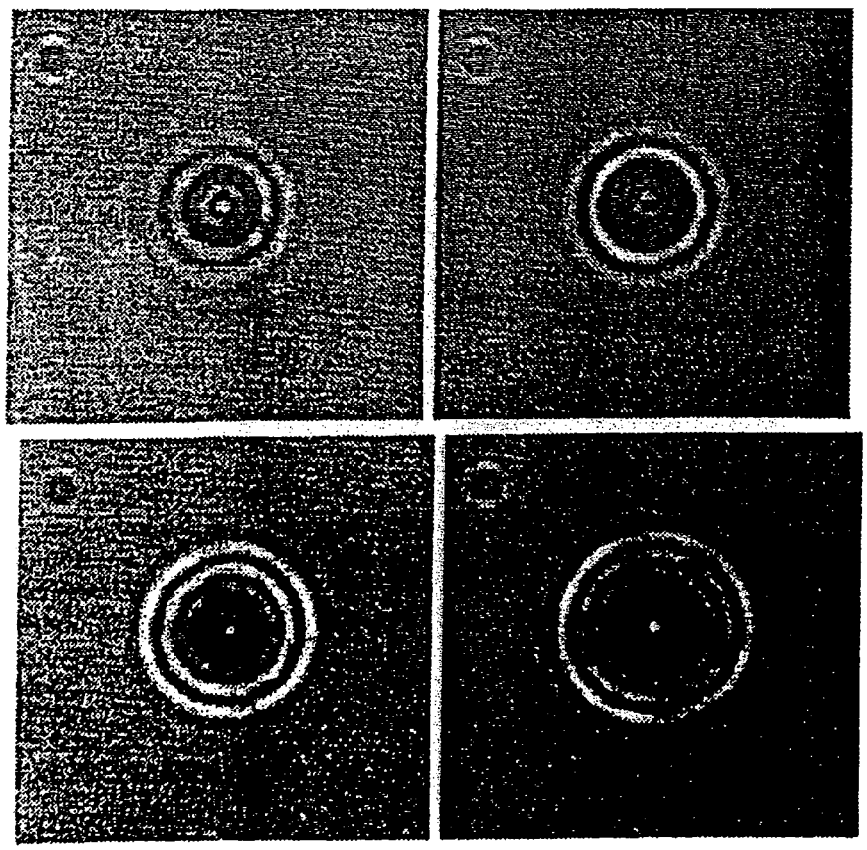
FIG. 3 presents the images of a bead at four positions.

The images of a bead at 4 positions equally spaced by 1 μm are presented on FIG. 3. Each image is characteristic of the position of the bead relative to the focal plane. Thus during the real-time acquisition, the light is averaged over circles and the intensity profile obtained is compared to a set of calibrated profiles to get the bead z position. The set of calibrated profiles is obtained by two operations. First at high force, the DNA is fully streched and thus the bead is quite immobile. A set of profiles is then stored. It is at this time possible to get the position of the bead relative to the focal plane. Second, to get the bead's absolute position the force is removed (by removing the magnets). The bead is then on the glass surface because of its weight. The average of this motion will give the anchoring point and will be removed from every extension point to get the absolute position of the bead.

Analysis of the Brownian Motion and Determination of the Force

When the bead is subjected to a force F and is tethered by a DNA of length l, it has positional (Brownian) fluctuations.

From the three dimensional positions of the bead as a function of time x(t), y(t), z(t), determined by the computer 4, different results are calculated by the computer 4 through the determination of the first statistical moments $<x>$, $<y>$, $<z>$, and $<x^2>$, $<y^2>$, $<z^2>$, and thus of the bead's fluctuations $\delta x^2$, $\delta y^2$, $\delta z^2$, and of the extension of the molecule l from the bead's position at F=0: $<x_0>$, $<y_0>$, $z_0>$.

In particular, the characteristics of the motion allow the measurement of the force applied to the bead and thus to the molecule.

Figure 4:
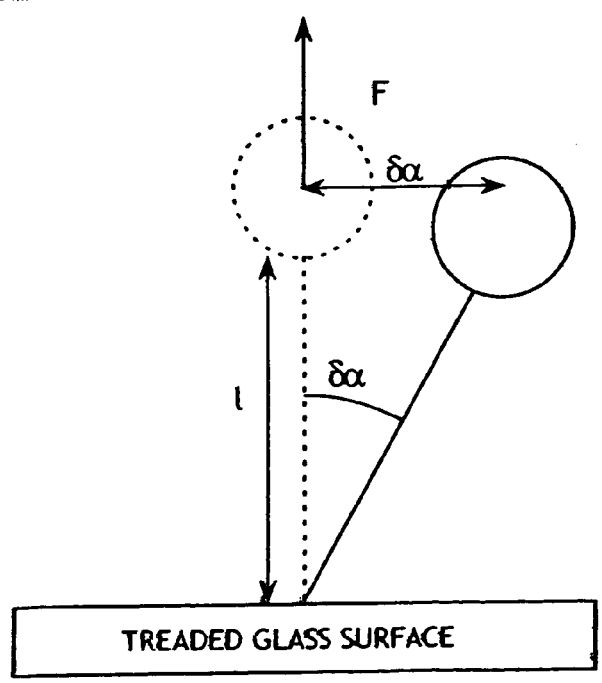
FIG. 4 is a schematic drawing on which the $\delta x$ and $\delta \alpha$ displacement parameters of a molecule have been presented.

When the bead moves from its equilibrium position it is subjected to restoring forces. In the direction of the force z, and of the molecule, the bead is brought back to its equilibrium position by the elasticity of the molecule. In the linear approximation this restoring force is just:

$$F_Z = \left(\frac{\partial F}{\partial l}\right)_l \delta z \qquad (1)$$

where δz is the length fluctuation of the molecule. In the xy plane perpendicular to the force, there is rotational invariance. If δx is the bead displacement from its equilibrium position in the x direction, δα the angle between the axis of he molecule and its axis when at equilibrium (as represented on FIG. 4) then the transverse restoring force $F_X$ is:

$$Fx = F\sin(\delta\alpha) \sim \frac{F}{1}\delta x \quad (2)$$

This relation is here derived as a first order approximation and one may think that it is true for only quite large extension (or small angle) of the molecule. However, C. Bouchiat proved t-hat it holds true even for small extension, l.

The transverse restoring force is the force proportional to the displacement fluctuation $\delta x$.

One can then define a spring with an effective constant $K_X = F/l$ and $$K_Z = \left(\frac{\partial F}{\partial l}\right)$$

and use the equipartition theorem to measure $K_\perp$ and $K_{//}$.

$$\frac{1}{2}K_X\langle\delta x^2\rangle = \frac{1}{2}K_B T \quad (3)$$

$$\frac{1}{2}K_Z\langle\delta z^2\rangle = \frac{1}{2}K_B T \quad (4)$$

From Eq.3 the force is given by the relation:

$$F = \frac{K_a T l}{\langle\delta x^2\rangle} \quad (5)$$

As said before the force measurement is thus reduced to a length (fluctuations and extension) measurement. As one knows $K_B T$, one can measure $\langle\delta x^2\rangle$ and l with the microscope and computer and calculate the force.

The previous discussion allows one to get the force versus extension, curve F(l), (by considering the xy fluctuations) and its first order derivative (by the z fluctuations).

This approach is very simple but the frequency analysis of the motion yields more information and allows for experimental improvements.

The equation of motion of the bead along any axis is:

$$m\frac{d^2 w}{dt^2} = F_L - K_w w - \gamma\eta R\frac{dw}{dt} \quad (6)$$

where w is the coordinate along this axis and $K_w$ the corresponding spring constant and where $F_L$ is the well known Langevin force characterized by:

$$\langle F_L \rangle = 0 \quad (7)$$

$$\langle F_L(t)F_L(t')\rangle = \delta(t-t') \quad (8)$$

and $\gamma$ the viscous drag coefficient ($6\pi$ for a bead in an infinite volume).

In frequency space the fluctuation-dissipation theorem gives:

$$w(\omega) = \frac{\sqrt{4K_B T\gamma\eta R}}{-m\omega^2 + K_w + i\gamma\eta R\omega} \quad (9)$$

The inertial term implies frequencies $$\frac{\gamma\eta R}{m} \text{ and } \sqrt{\frac{K_w}{m}}$$

that are in the KHz range and thus not accessible in the experimental setup limited by the video frequency. As they are filtered out, the remaining terms are:

$$|w(\omega)|^2 = \frac{\frac{4K_B T\gamma\eta R}{K_w}}{1+\left(\frac{\omega}{\omega_C}\right)^2} \quad (10)$$

with $$\omega_c = \frac{K_w}{\gamma\eta R}.$$

This power spectrum is then Lorentzian with white noise at low frequencies, whose amplitude is regulated by the force, and is filtered at high frequencies by the viscosity. The cutoff frequency is determined by the ratio of the effective spring constant and the viscous drag term. Integration of that spectrum yields:

$$\frac{1}{2\pi}\int_o^\infty |W(\omega)^2|d\omega = \lim\frac{1}{T}\int_o^T x^2(t)dt = \frac{K_3 T}{K_W} \quad (11)$$

The main advantage of the frequency analysis is that one may get rid of slow drifts by analyzing only the frequencies larger than some threshold value.

The second advantage is that one can test that the cutoff frequency is not too high (<25 Hz) for the experimental setup so that unwanted filtering does not occur during the video acquisition. One can also check that there are enough modes below this frequency to have good statistics. To measure very low forces with precision one has to wait for a long time (about 40 minutes for F~0.01 pN).

Knowing the cutoff frequency and K the spring constant, one can find the viscous drag on the system:

$$\gamma = \frac{K}{\eta R\omega_c}$$

The system is modeled as a bead of radius R attached by a cylinder of radius R' (~$10^{-9}$ m at high extension) and length l. The viscous drag on the bead is:

$$F_{Bead} = 6\pi\eta R\left[1+\frac{9R}{16l}\right] \quad (12)$$

The viscous force active on a cylinder of length l with a speed U in an infinite medium is:

$$F_{cyl} = \frac{4\pi\eta lU}{\frac{1}{2} - C_{euler} - \text{Ln}\left(\frac{R'U}{4v}\right)} 0.4\eta lU \quad (13)$$

assuming that the viscous drag on the DNA molecule is $$F_{DNA} = \frac{F_{cyl}}{2}$$

because of the presence of the glass surface implying U=0 on it, the total viscous drag on our system is:

$$\gamma = 6\pi\eta R\left[1 + \frac{9R}{16l} + \frac{0.4}{6\pi R}\right] \quad (14)$$

The experimental results are in accord with the theoretical predictions to within a few percent. By measuring this drag coefficient which has been theoretically determined and by controlling the agreement one can check the acquisition chain.

Figure 5:
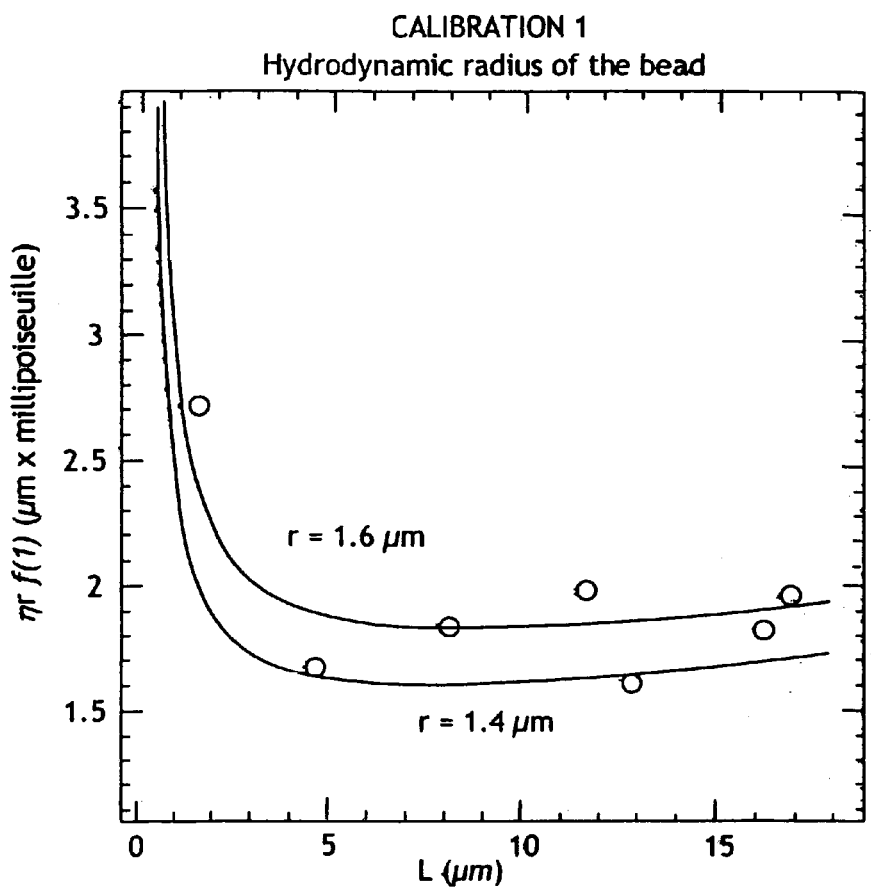
FIG. 5 is a graph in which the viscous drag of DNA molecules has been presented as a function of the distance between the bead and the surface on which the molecule is attached.

The viscous drag has been measured from the cutoff frequency. The results are given on FIG. 5. As the force increases, the distance between the bead and the surface is also increasing. The viscous drag is a function of that distance. The presence of the DNA also influences its value. The inventors modeled the system as a bead of radius R (1.4 µm) at a distance d from a surface attached by a cylinder of radius R' and length l. The full lines are the calculated values for R equal to 1.4 or 1.6 µm (see Eq. 14) and the dots are the experimental data. One can see that the agreement is good and then that the acquisition chain works well.

Anchoring of the Molecule to the Bead and to the Surface

Figure 6:
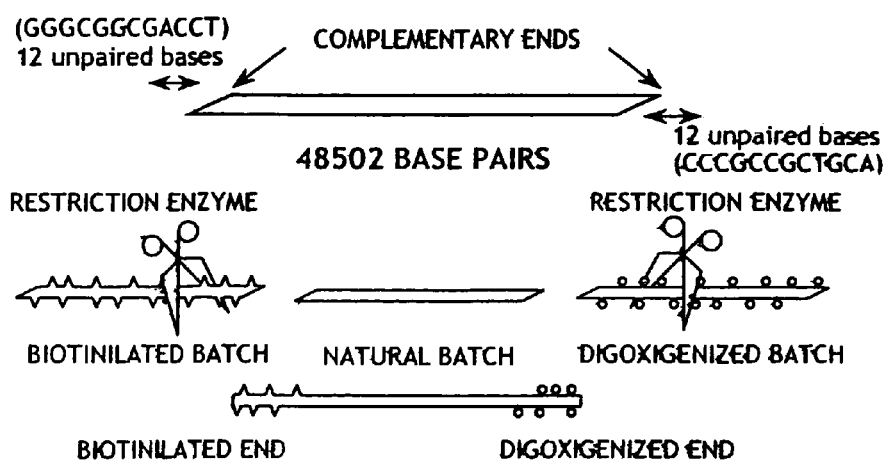
FIG. 6 illustrates the multiple anchoring of a DNA molecule.

Multiple anchoring points at each extremity of the molecule are used in the exoeriment, see FIG. 6, to catch the molecule in such a way that free rotation around a single link is avoided.

In the example shown on FIG. 6, the DNA molecules are from phage-λ (48502 base pairs). This DNA has the specificity of having 12 unpaired bases at its extremities. The bases from one extremity are complementary to the ones of the other. This gives it the ability to circularise. The molecules are divided in three batches. The first one is photochemically and randomly labelled with biotin and cut at a specific site with a restriction enzyme. The second is in the same way labelled with digoxigenin and cut. The extremities of those two batches of molecules are separated electrophoretically. A selected extremity of the first batch and the third one (which is unlabeled and uncut) are mixed. With its complementary unpaired bases the biotinylated DNA links to the end of the unlabeled one. This construct is mixed with the extremity of the digoxigeni labelled batch (2) which is complementary to the unbiotinilated end of DNA in batch 3. The final construct is then a DNA, ~20 µm long, with ~1.5 µm covered with biotin and ~1.5 µm labelled with digoxigenin. This construct allows us to catch a single DNA molecule between a streptavidin covered bead and an anti-digoxigenin coated glass surface.

Elasticity of DNA

Because of great improvements in the biochemistry of DNA it is now possible to catch a DNA molecule by its extremities, see FIG. 1. With this ability to manipulate single molecules of DNA it has become possible to measure for the first time the elasticity of a single DNA. The work of C. Bustamante (C. Bustamante, S. F. Marcko, E. D. Siggia and S. Smith, Science, 265: 1599–1600; 1994) demonstrated that DNA follows the Worm Like Chain model of a polymer.

The simplest model of a polymer is the freely jointed chain model. It considers the different segments of the molecules as independent, like the steps of a random walk. For long or flexible polymers the steric repulsion allows only self avoiding random walks but the DNA molecules used in this paper are not very long so self avoidance is irrelevant. The partition function of such a polymer under traction can be easily calculated. It yields for the force extension curve the reverse of a Langevin function:

$$F = \frac{K_B T}{A} L^{-1}\left(\frac{1}{l_0}\right) \quad (15)$$

where l is the end to end distance of the molecule, $l_O$ is the crystallographic length and A is the persistence length: the length over which thermal fluctuations can bend a molecule (it is the equivalent of the step size in a random walk).

This force is purely entropic and is due to the reduction of the number of accessible conformations. In the Worm Like Chain model additional curvature energy must be considered. Hence the energy of the polymer under traction is given by:

$$\frac{E}{K_B T} = \int_0^{l_0}\left[\frac{A}{2}(\partial_s(r))^2 ds\right] - \frac{F}{K_B T}l \quad (16)$$

where $\partial_s(r)$ is the curvature. So the elasticity of the molecule is not only due to entropic effect as in the freely joint chain model. The force extension curve has been calculated in this model. In standard salt conditions A has been measured and is ~53 nm which yields for the scaling force $$\frac{K_B T}{A} - 0.08 pN$$

Those results will be used to determine if one or more DNA molecules are attached to the beads.

The DNA polymer has a specificity. DNA is made up of two complementary strands and this property gives it a unique torsional behavior. The biological implications (in terms of replication for instance) of the two strands are famous but their topological and the resulting mechanical effects are less known.

The two strands can not cross each other. That means that the two strands can not rotate one around each other if maintained at their extremities. This is not the same for commonly used polymers, like polystyrene, where rotation around chemical links makes free rotation possible.

Since the two strands cannot cross, when one applies torsion to DNA, one generates solenoids or plectonemes (those structures that one has already seen on twisted telephone cords). The plectonemes appear in order to relax the torsional stress. The constraint is then transfered into bending. Common experiments with telephone cords give similar results: the rigidity increases with rotation and the plectonemes which shorten the apparent length are present at low forces but not at high forces. In DNA however, the effects of torsion are not only mechanical; they also play an important role in the biological activity of the molecule and extensive work has been published on this topic. For example, the unwinding of the helix is supposed to facilitate the opening of DNA and to allow transcription of DNA. The transcription itself generates unwound DNA behind the protein that transcribes (the polymerase) and overwound DNA in front of it. The basic physical components needed to understand the behavior of supercoiled DNA are:

- the curvature energy as for the usual Worm Like Chain model.
- the torsionnal spring constant of the molecule. As for a rope or wire it costs energy to apply torsion to the molecule. This effect is characterised by a torsionnal spring constant.
- the electrostatic repulsion. For example in plectonemes two parts of the molecule can be brought close one to the other. The electrostatic repulsion between the two negatively charged parts of the molecule then increases the effective steric repulsion between the two double strands. This effect is dependent on the screening of the electrostaic charges and thus of the salt concentration in the solution.
- The thermal activation which tends to increase the entropy of the molecule.

J. Marko and E. Siggia proposed a theoretical model. They calculate the energy of two particular forms: the plectoneme and the solenoidal form. They minimize the energy with respect to the partition between the two forms.

Experimental Tests and Results

The DNA molecules used in the experimental results presented are from the phage λ, a small virus. It is 48502 base pairs long. Its length is 16.2 µm and its natural number of turns is about 5000. The DNA is differentially labeled with ligands at its extremities. The final construct is then 20 µm long with 16.2 µm unlabelled. For the experiment that implies that the length of the molecule between the attachment points can vary from 16.2 to 20 µm and that the crystallographic length between those points has to be measured for each molecule. To compare different molecules the relative extension is used. It is the ratio of the end to end extension of the molecule divided by its crystallographic length.

In the experimental setup the magnets which are used to apply the force (by translating them) are also used to control the orientation of the superparamagnetic bead. With a motor one may rotate the magnets about the optical axis. The rotation of the bead is exactly the same as that of the magnets. In this way one turns the bead by a desired number of turns and in a reversible manner allowing for torsional control of DNA.

Figure 7:
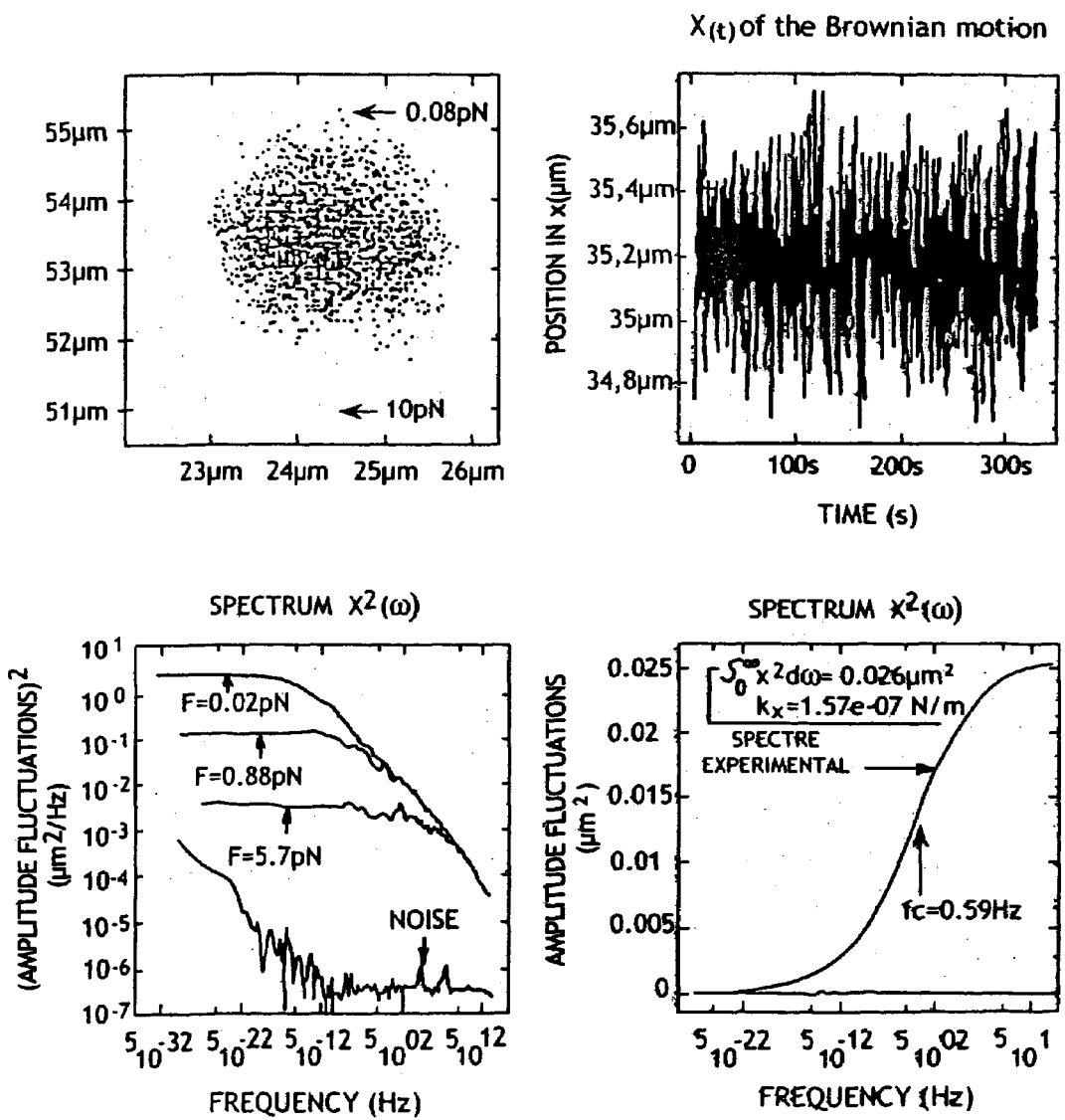
FIG. 7 presents four graphs illustrating the treatment by the computer of a recording of the bead's Brownian motion.

An example of a treatment by the computer 4 on a recorded Brownian motion is given on FIG. 7. The x and y movements are extracted. The average and the fluctuations of the motion are calculated. The power spectrum of the fluctuations is then determined. One may see that the amplitude of the spectrum is a decreasing function of the force and that the cutoff frequency is an increasing function of it. The noise curve has been determined from the movement of a deliberately glued bead. A filter is applied to the spectrum to remove the drifts of the microscope and the result is integrated and fitted with an Argtang function to evaluate the cutoff frequency and the limit. This limit is then multiplied by the length to get the force.

The Brownian motion analysis allowed measurements in the whole relevant force regime for DNA and is sensitive enough to distinguish very small changes in its elastic behavior. In particular small changes in its torsion can be detected.

First of all it is possible to distinguish different cases where one, two, or one long and one short molecules are attached to a bead. If the bead is attached by just one molecule, its persistence length is, in the ionic conditions presented here (10 mM phosphate ions), 53 nm. If one has two molecules attached to one bead, and if their attachment points are not too far one from the other, the length of the molecule will be the same but the rigidity will be twice as great, as for two parallel springs. If one defines an effective persistence length as the persistence length of an equivalent single molecule following the Worm Like Chain model, it will be in this case twice as short ~26.5 nm. Now if one has a bead attached by one molecule plus a dimer (two concatenated molecules whose presence can not be totally eliminated), the rigidity will increase and the effective persistence length of the Worm Like Chain that fits the data will be 44 nm. So the system can determine how many molecules are attached to a bead.

Figure 8:
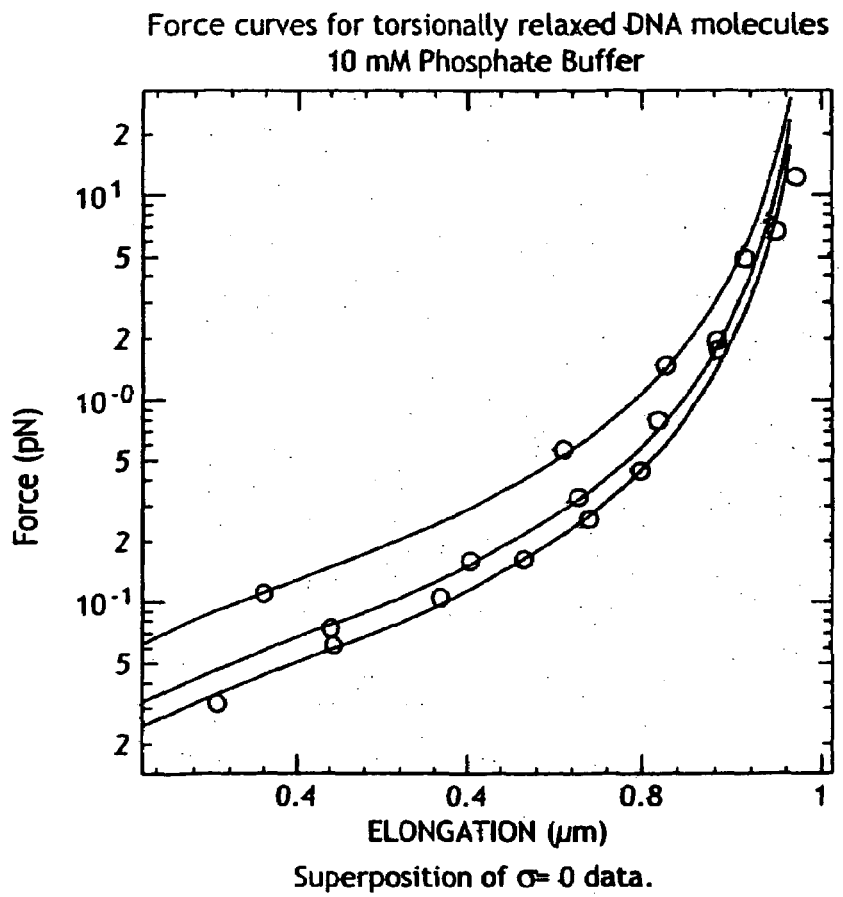
FIG. 8 is a graph in which force curves for torsionally relaxed DNA molecules are presented.

This is shown on FIG. 8 where different cases are presented. a) a bead attached by one molecule. b) a bead attached by two molecules c) a bead attached by a monomer plus a dimer. The experimental points are placed sufficiently close to their theoretical curve that one is able to discriminate between the different cases.

Figure 9:
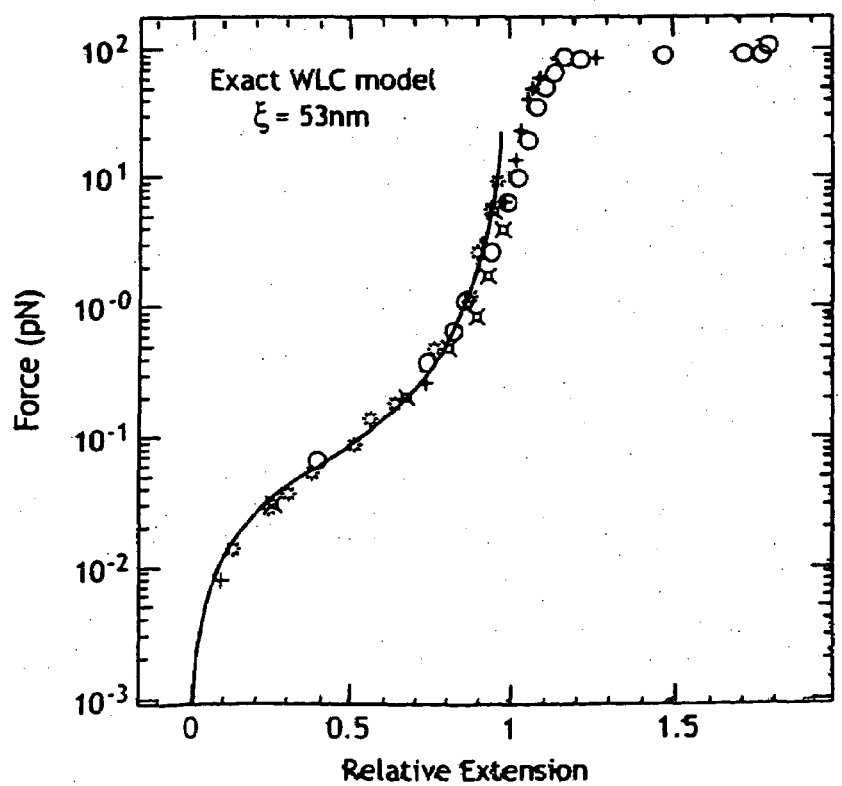
FIG. 9 is a graph in which force curves for different DNA molecules are superposed.

Second, as shown on FIG. 9, forces have been measured from 6 fN to more than 100 pN. The dynamic of the system is then of 5 decades. It goes from the entropic range of DNA extension, where the force applied just reduces the number of configurations that the molecule can sample (that is scaled by $$\frac{K_B T}{A} - 0.08 pN$$

as previously discussed), to its elastic regime, where the stress is strong enough to deform the bonds of the molecule (and even to induce a phase transition). The forces of biological motors acting on DNA are exactly in the range explored (enzymes that transcribe DNA into RNA still work when pulled at 14 pN, other proteins are known to lengthen DNA by a factor of ~1.5). So the system can measure forces in the most important range of forces for biophysical studies on single molecules.

On the example shown on FIG. 9, the whole range of forces explored is presented. The points are from different molecules. To reach very high forces (>50 pN) bigger beads (4.5 µm) are used. The abrupt transition in extension corresponds to the transition to the S form of DNA that has been recently discovered. This DNA structure appears at high forces ~70 pN in 10 mM phosphate buffer. At this force there is an abrupt transition were the DNA extension is multiplied by 1.6 as DNA goes from B (the usual DNA form in standard solution conditions), to S form. The system can also measure smaller forces. In the range 20 pN<F<70 pN is the elastic regime of DNA where the stress is applied to the chemical bonds. Even lower forces correspond to the entropic regime discussed earlier. To measure the very low forces with precision one has to wait for ~90 minutes whereas each point at high forces requires less than 1 minute.

This system allowed for the first time to measure the elasticity of a single torsionally constrained DNA molecule. It is very sensitive to the number of turns applied to the molecule. As said before the DNA molecules used are about 16.2 μm long and have about 5000 natural turns in their helical structure. The amount of turns imposed varies from −25000 to 15000.

Figure 10:
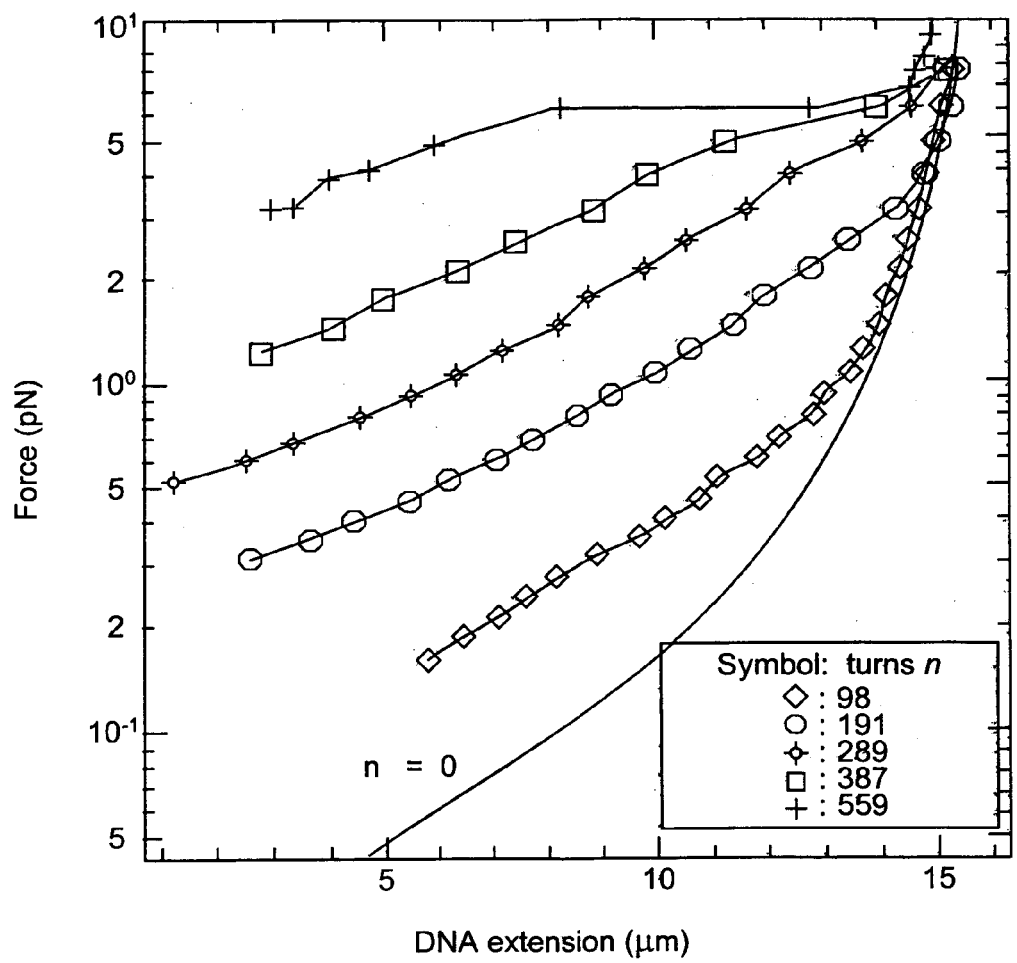
FIG. 10 and FIG. 11 are graphs presenting force curves for, respectively, positively and negatively supercoiled DNA.
Figure 11:
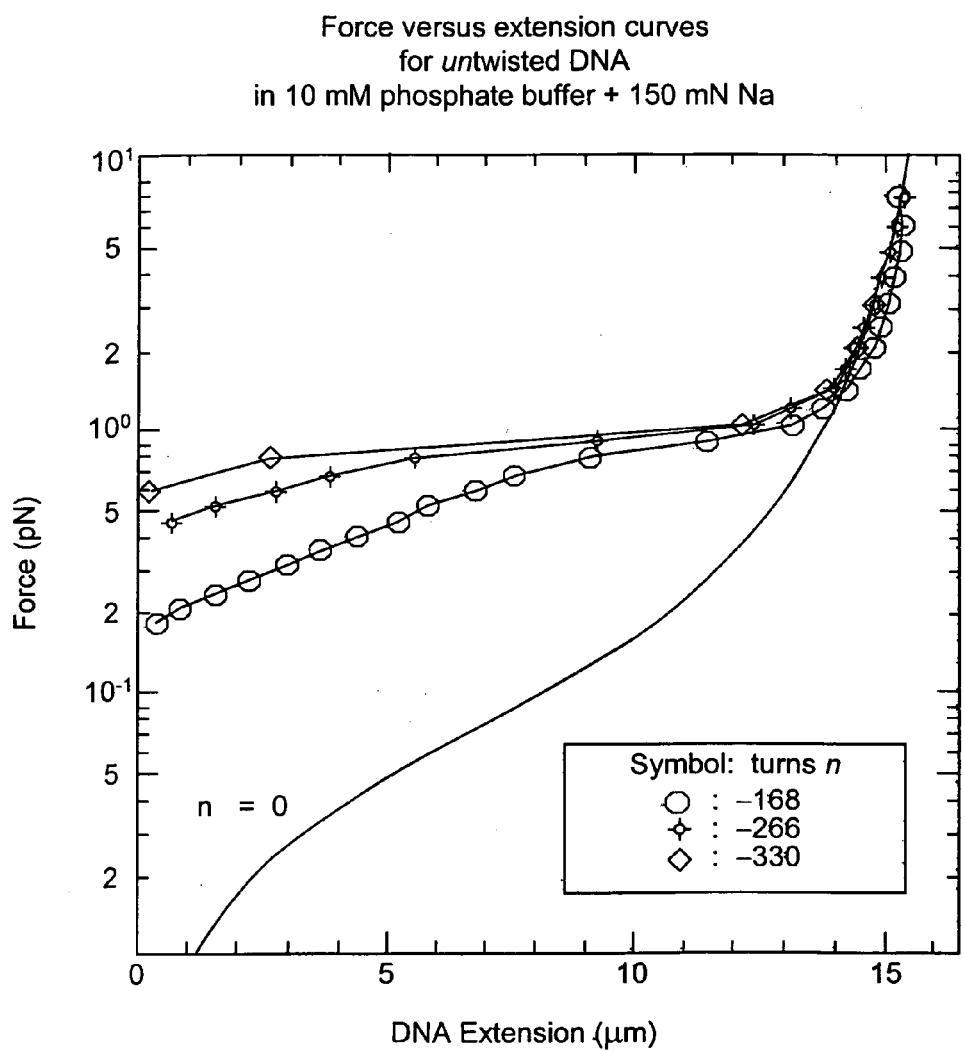

Different elasticity curves have been obtained at 25° C. in 10 mM Phosphate buffer for different number of turns ,N. As can be deduced from common experience with telephone cords, the rigidity of the molecules is an increasing function of the number of turns. In FIG. 10 and FIG. 11 the elasticity of the molecules is presented as a function of the number of turns N. In these curves, critical forces appear differentially for positive and negative N (DNA is a right handed double helix). At these forces, 0.3 pN for negative N and 3 pN for positive N, the molecule goes from a low to a high extension state. This transition is sharp and so is associated with a first order phase transition. More precisely the inventors think that those forces correspond to transitions from B-DNA to other DNA forms. For positive N, this form should be naturally more coiled than B-DNA but it could not yet be identified. For negative N a bubble of denatured DNA appears, which means that in some parts of the molecule the hydrogen bonds between paired bases are broken and the two strands are then separated.

Figure 12:
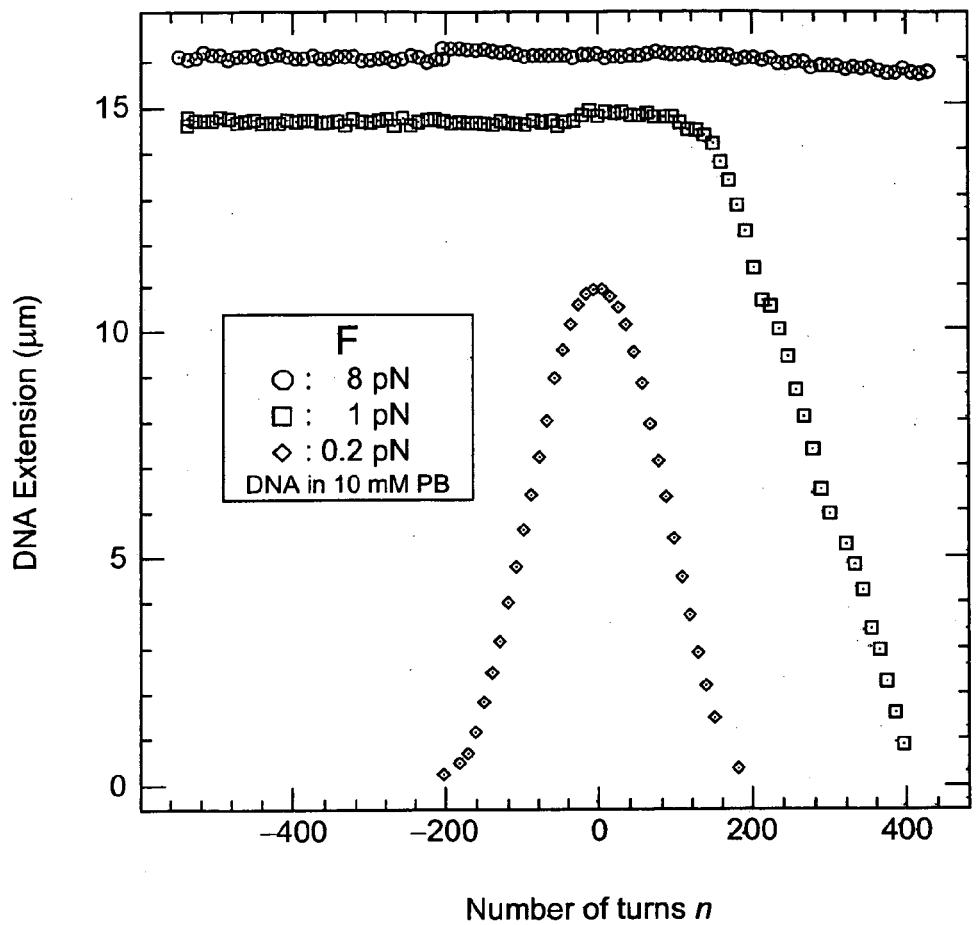
FIG. 12 is a graph presenting extension versus supercoiling curves for constant forces.

FIG. 12 presents the same results from a different point of view, where the chirality of the molecule can be more clearly seen. The molecule is now pulled at a constant force and the magnets are turned. The rigidity increases with the number of turns, and rotating the magnets causes the bead to descend to the surface (if the force is lower than the critical forces). To have a picture of what happens one may think that as the DNA is coiled, the molecule becomes more rigid and at the same time plectonemes appear. They absorb some of the length of the molecule and the molecule's extension decreases. At forces higher than the negative critical force the DNA shortens only for positive N. For negative N, the denaturation bubble that appears absorbs the additional turns and the molecule does not shorten anymore. For forces greater than the positive critical force, the bead does not go down to the surface because the applied torsion is absorbed by the new forms of DNA that are induced instead of creating plectonemes.

At small forces (0.3<pN) the curves present a linear regime. The slope is about 0.08 μm/turn. By considering results of electromicroscopy, a plectoneme has a radius of r=100 Å, a pitch of p=140 Å and a partition of 8 turns absorbed in the plectoneme for 10 added turns. It yields to an effective length decrease per turn of:

$$^2l = \sqrt{(2\pi r)^2 + p^2} \times 00.85 \text{ μm/turn} \quad (17)$$

which is consistent with our previous data: 0.08 μm/turn.

Thus as length variations of 0.1 μm can be detected the sensibility to supercoiling is about 1 turn. The system is sensitive enough to detect as little as 1 turn on a molecule comprising 5000. This is more sensitive than what is allowed by any other method. It is also the first which allows torsion on linear DNAs and not on circular DNAs as usual. It also has the advantage of being reversible.

Because of this sensitivity, the method can be used to probe the local nucleotide content of a DNA molecule and maybe even to sequence it.

As we have seen, a negatively coiled DNA molecule may partition its torsional constraint between a denatured bubble and a plectonemic part.

Our sensitivity of about one plectonemic turn translates to a sensitivity to denaturation of one turn of the double helix, namely 10 base pairs.

By monitoring the force or the extension of the molecule as it is wound, the inventors are now able to sense local variations in nucleotide content of about 10 base pairs.

By improving on the sensitivity of the present apparatus, in particular the length measurement, sensitivity to single nucleotide content, i.e. sequencing, could be achieved.

Figure 13:
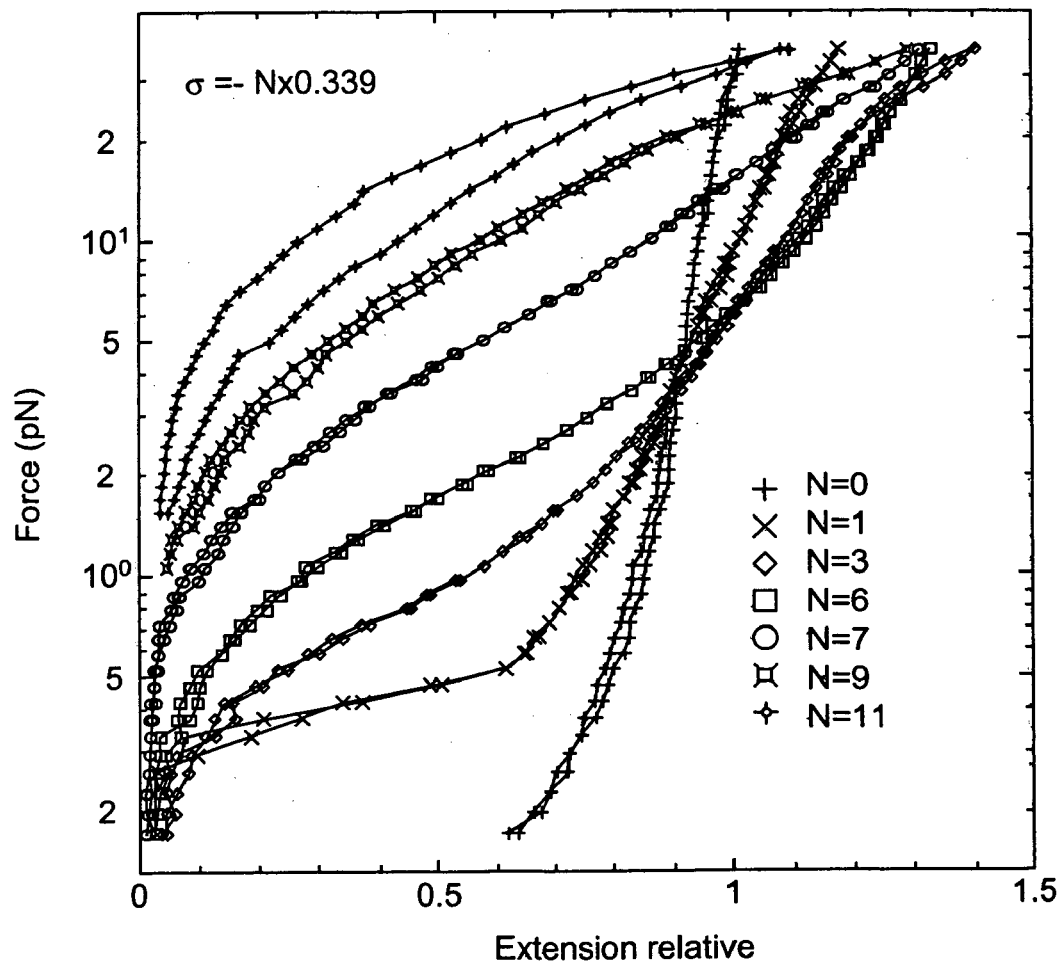
FIG. 13 is a graph presenting force curves for high degrees of supercoiling.

Moreover the methods previously used could not reach very high N (without changing drastically the solution properties). Here the only limit is the strength of the bonds between the DNA and its supports. N has been varied from 15000 to −25000. That means that if all the added turns were used to coil the molecule and not to create new DNA forms or plectonemes, it would have been coiled in the opposite sense of the natural double helix (N=−10000) or the pitch would have been twice shorter (N=+5000). At such high N internal mechanical effects can be detected. As one unwinds or overwinds a double helix one expects that in the first case the molecule would lengthen and shorten in the other. When underwinding the molecule one sees that the length increases with the number of turns. If a bond breaks and the molecule is free to rotate it returns back to its initial state and to its natural crystallographic length, see FIG. 13. Exactly the same thing happens for high positive N except that the length decreases.

Biotechnology Applications

Since the seventies, it is known that the winding of the DNA double helix is crucial for biological activity. For example, it is implicated in the control of genes, their replication and transcription. An underwound DNA is slightly uncoiled: the two branches of the double helix cross less often and it presents a higher helical step than for a DNA naturally wound. On the contrary, an overwound DNA presents a smaller helical step. A number of specialized enzymes—the topoisomerases—manage in vivo the winding of the DNA. In particular, the DNA is often underwound in the cellular nucleus, which facilitates its interaction with regulatory proteins.

The inactivation of a topoisomerase II in eukaryotes can lead to chromosomal aberration during the course of cellular division. By slowing the growth and division of cells, the inhibitors of topoisomerases present anticancer, antibacterial and antiviral activities.

The method proposed here permits one to study the interactions of a DNA with proteins such as topoisomerases and could lead to the development of efficient drugs against topoisomerases. For anticancer or antibacterial activities, for example, a DNA molecule can be selected in the apparatus and a topoisomerase can be added to it. The proposed method permits the study of the relation between its extension and its winding. From the DNAs extension one may thus infer the activity of the topoisomerase.

In an other possible application—leading to the selection and development of antibacterial, antiviral or anticancer agents inhibiting topoisomerase activity—a quantitative control of the DNA winding could bring to a better characterization of the topoisomerase inhibitors. More generally, the technique proposed could be used to study DNA-DNA or DNA-proteins (such as recA or ligase for example) which can influence the conformation of DNA.

The invention claimed is:

1. An apparatus for manipulating and testing molecules comprising:

(A) a surface to which a molecule is anchored at one or more points proximate to a first extremity of the molecule;
(B) a paramagnetic bead on which the molecule is anchored at one or more points proximate to a second extremity of the molecule, the surface being an internal surface of a capillary tube in which solutions are injected;
(C) a magnetic means for providing a magnetic field to thereby apply a force to the bead, said magnetic means being arranged such that the bead is maintained by the force at a distance from the surface;
(D) an optical magnification means having an optical axis and a camera for capturing images of the bead; and
(E) a computer means to which the images from the camera are transmitted, said computer means being configured to compute the position of the bead in three spatial directions (x,y,z) and the fluctuation (δx,δy,δz) of the position of the bead in the three spatial directions, the computer means also being configured to analyze the diffraction pattern of the bead to determine a position of the bead along the z direction of the optical axis of the magnification means.

2. The apparatus according to claim 1, wherein the computer means is configured to:
(A) follow Brownian motion of the bead in the x, y plane perpendicular to the direction z of the force applied to the bead;
(B) measure the molecule length l, in the direction z of the force applied to the bead;
(C) determine the mean value <δx> or <δy> of the fluctuations δx and δy of the bead; and
(D) calculate the value of the force F $$F = \frac{K_B T l}{\langle \delta x^2 \rangle} \text{ or } F = \frac{K_B T l}{\langle \delta y^2 \rangle}$$

where F is the force applied to the bead, $K_B$ is the Boltzman constant, T is the ambient temperature, and l is the length of the molecule.

3. The apparatus according to claim 2, wherein the computer means is configured to verify that $\delta x^2 \approx \delta y^2$.

4. The apparatus according to claim 1, wherein the computer means is configured to compare, in real time, a diffraction pattern of the bead to a reference set of diffraction patterns.

5. The apparatus according to claim 4, wherein the reference set of diffraction patterns is previously built at 20 pN to 70 pN.

6. The apparatus according to claim 1, wherein intensity profiles of diffraction patterns are obtained by averaging light levels over circles centred on the bead.

7. The apparatus according to claim 1, wherein means to control the ambient temperature of the molecule and bead are provided.

8. The apparatus according to claim 1, wherein the molecules are DNA molecules.

9. The apparatus according to claim 1, wherein the computer means is configured to:
(A) compute the length l of the molecule, and
(B) calculate the value of the force F $$F = \frac{K_B T l}{\langle \delta x \rangle^2} \text{ or } \frac{K_B T l}{\langle \delta y \rangle^2}$$

where F is the force applied to the bead, $K_B$ is the Boltzman constant, T is the ambient temperature, and l is the length of the molecule.

10. The apparatus according to claim 1, further comprising:
(F) a rotating means for spinning the magnetic means about the optical axis of the optical magnification means, wherein the magnetic means is positioned at a distance from the molecule in the direction of the optical axis of the optical magnification means, perpendicular to the optical axis, such that
(i) the force applied to the bead is substantially directed parallel to the optical axis; and
(ii) the field produced by the magnetic means is perpendicular to the optical axis,
wherein the magnetic means can be moved for controlling translation and rotation of the bead, to thereby control stretching and torsion of the molecule.

11. An apparatus for manipulating and testing molecules comprising:
(A) a surface to which a molecule is anchored at one or more points proximate to a first extremity of the molecule;
(B) a paramagnetic bead on which the molecule is anchored at one or more points proximate to a second extremity of the molecule;
(C) a magnetic means for providing a magnetic field to thereby apply a force to the bead, said magnetic means being arranged such that the bead is maintained by the force at a distance from the surface;
(D) an optical magnification means having an optical axis and a camera for capturing images of the bead;
(E) a computer means to which the images from the camera are transmitted, said computer means being configured to compute the position of the bead in three spatial directions (x,y,z) and the fluctuation (δx,δy,δz) of the position of the bead in the three spatial directions; and
(F) a means to control the ambient temperature of the molecule and the bead, the computer means also being configured to analyze the diffraction pattern of the bead to determine a position of the bead along the z direction of the optical axis.

12. The apparatus according to claim 11, wherein the computer means is configured to:
(A) follow Brownian motion of the bead in the x, y plane perpendicular to the direction z of the force applied to the bead;
(B) measure the molecule length l, in the direction z of the force applied to the bead;
(C) determine the mean value <δx> or <δy> of the fluctuations δx and δy of the bead; and
(D) calculate the value of the force F $$F = \frac{K_B T l}{\langle \delta x \rangle^2} \text{ or } \frac{K_B T l}{\langle \delta y \rangle^2}$$

where F is the force applied to the bead, $K_B$ is the Boltzman constant, T is the ambient temperature, and l is the length of the molecule.

13. The apparatus according to claim 12, wherein the computer means is configured to verify that $\delta x^2 \approx \delta y^2$.

14. The apparatus according to claim 11, wherein the computer means is configured to compare, in real time, a diffraction pattern of the bead to a reference set of diffraction patterns.

15. The apparatus according to claim 14, wherein the reference set of diffraction patterns is previously built at 20 pN to 70 pN.

16. The apparatus according to claim 11, wherein intensity profiles of diffraction patterns are obtained by averaging light levels over circles centred on the bead.

17. The apparatus according to claim 11, wherein the molecules are DNA molecules.

18. The apparatus according to claim 11, wherein the computer means is configured to:
(A) compute the length l of the molecule, and
(B) calculate the value of the force F $$F = \frac{K_B Tl}{<\delta x^2>} \text{ or } \frac{K_B Tl}{<\delta y^2>}$$

where F is the force applied to the bead, $K_B$ is the Boltzman constant, T is the ambient temperature, and l is the length of the molecule.

19. The apparatus according to claim 11, further comprising:
(G) a rotating means for spinning the magnetic means about the optical axis of the optical magnification means, wherein the magnetic means is positioned at a distance from the molecule in the direction of the optical axis of the optical magnification means, perpendicular to the optical axis, such that
  (i) the force applied to the bead is substantially directed parallel to the optical axis; and
  (ii) the field produced by the magnetic means is perpendicular to the optical axis,
wherein the magnetic means can be moved for controlling translation and rotation of the bead, to thereby control stretching and torsion of the molecule.

20. An apparatus for manipulating and testing molecules comprising:
(A) a surface to which a molecule is anchored at one or more points proximate to a first extremity of the molecule;
(B) a paramagnetic bead on which the molecule is anchored at one or more points proximate to a second extremity of the molecule;
(C) a magnetic means for providing a magnetic field to thereby apply a force to the bead, said magnetic means being arranged such that the bead is maintained by the force at a distance from the surface;
(D) an optical magnification means having an optical axis and a camera for capturing images of the bead;
(E) a computer means to which the images from the camera are transmitted, said computer means being configured to compute the position of the bead in three spatial directions (x,y,z) and the fluctuation ($\delta x, \delta y, \delta z$) of the position of the bead in the three spatial directions, the computer means also being configured to analyze the diffraction pattern of the bead to determine a position of the bead along the z direction of the optical axis of the magnification means.

21. The apparatus according to claim 20, wherein the computer means is configured to:
(A) follow Brownian motion of the bead in the x, y plane perpendicular to the direction z of the force applied to the bead;
(B) measure the molecule length l, in the direction z of the force applied to the bead;
(C) determine the mean value $<\delta x>$ or $<\delta y>$ of the fluctuations $\delta x$ and $\delta y$ of the bead; and
(D) calculate the value of the force F $$F = \frac{K_B Tl}{<\delta x^2>} \text{ or } \frac{K_B Tl}{<\delta y^2>}$$

where F is the force applied to the bead, $K_B$ is the Boltzman constant, T is the ambient temperature, and l is the length of the molecule.

22. The apparatus according to claim 21, wherein the computer means is configured to verify that $\delta x^2 \approx \delta y^2$.

23. The apparatus according to claim 20, wherein the computer means is configured to compare, in real time, a diffraction pattern of the bead to a reference set of diffraction patterns.

24. The apparatus according to claim 23, wherein the reference set of diffraction patterns is previously built at 20 pN to 70 pN.

25. The apparatus according to claim 20, wherein intensity profiles of diffraction patterns are obtained by averaging light levels over circles centred on the bead.

26. The apparatus according to claim 20, wherein the molecules are DNA molecules.

27. The apparatus according to claim 20, wherein the computer means is configured to:
(A) compute the length l of the molecule, and
(B) calculate the value of the force F $$F = \frac{K_B Tl}{<\delta x^2>} \text{ or } \frac{K_B Tl}{<\delta y^2>}$$

where F is the force applied to the bead, $K_B$ is the Boltzman constant, T is the ambient temperature, and l is the length of the molecule.

28. The apparatus according to claim 20, further comprising:
(F) a rotating means for spinning the magnetic means about the optical axis of the optical magnification means, wherein the magnetic means is positioned at a distance from the molecule in the direction of the optical axis of the optical magnification means, perpendicular to the optical axis, such that
  (i) the force applied to the bead is substantially directed parallel to the optical axis; and
  (ii) the field produced by the magnetic means is perpendicular to the optical axis,
wherein the magnetic means can be moved for controlling translation and rotation of the bead, to thereby control stretching and torsion of the molecule.

* * * * *

UNITED STATES PATENT AND TRADEMARK OFFICE
CERTIFICATE OF CORRECTION

PATENT NO. : 7,052,650 B2
APPLICATION NO. : 10/163089
DATED : May 30, 2006
INVENTOR(S) : Terrence R. Strick et al.

It is certified that error appears in the above-identified patent and that said Letters Patent is hereby corrected as shown below:

On the title page, item (57), line 9, "visualisation" should read --visualization--.

Title page, item (73), "Center" should read --Centre--.

In claim 2, column 13, line 31, "length I," should read --length 1,--.

In claim 2, column 13, lines 38-40, " $F = \dfrac{K_B Tl}{\langle \delta x^2 \rangle}$ or $F = \dfrac{K_B Tl}{\langle \delta y^2 \rangle}$ " should read -- $F = \dfrac{K_B Tl}{<\delta x^2>}$ or $\dfrac{K_B Tl}{<\delta y^2>}$ --.

In claim 6, column 13, line 57, "centred" should read --centered--.

In claim 9, column 14, lines 1-4, " $F = \dfrac{K_B Tl}{<\delta x>^2}$ or $\dfrac{K_B Tl}{<\delta y>^2}$ " should read -- $F = \dfrac{K_B Tl}{<\delta x^2>}$ or $\dfrac{K_B Tl}{<\delta y^2>}$ --.

In claim 12, column 14, line 56, "length I," should read --length 1,--.

In claim 12, column 14, lines 63-65, " $F = \dfrac{K_B Tl}{<\delta x>^2}$ or $\dfrac{K_B Tl}{<\delta y>^2}$ " should read -- $F = \dfrac{K_B Tl}{<\delta x^2>}$ or $\dfrac{K_B Tl}{<\delta y^2>}$ --.

In claim 16, column 15, line 15, "centred" should read --centered--.

UNITED STATES PATENT AND TRADEMARK OFFICE
CERTIFICATE OF CORRECTION

PATENT NO. : 7,052,650 B2
APPLICATION NO. : 10/163089
DATED : May 30, 2006
INVENTOR(S) : Terrence R. Strick et al.

It is certified that error appears in the above-identified patent and that said Letters Patent is hereby corrected as shown below:

In claim 18, column 15, lines 24-26, " $F = \dfrac{K_B Tl}{2<\delta x>}$ or $\dfrac{K_B Tl}{2<\delta y>}$ " should read -- $F = \dfrac{K_B Tl}{<\delta x^2>}$ or $\dfrac{K_B Tl}{<\delta y^2>}$ --.

In claim 21, column 16, line 8, "length I," should read --length 1,--.

In claim 21, column 16, lines 14-16, " $F = \dfrac{K_B Tl}{2<\delta x>}$ or $\dfrac{K_B Tl}{2<\delta y>}$ " should read -- $F = \dfrac{K_B Tl}{<\delta x^2>}$ or $\dfrac{K_B Tl}{<\delta y^2>}$ --.

In claim 25, column 16, line 33, "centred" should read --centered--.

In claim 27, column 16, lines 42-44, " $F = \dfrac{K_B Tl}{2<\delta x>}$ or $\dfrac{K_B Tl}{2<\delta y>}$ " should read -- $F = \dfrac{K_B Tl}{<\delta x^2>}$ or $\dfrac{K_B Tl}{<\delta y^2>}$ --.

Signed and Sealed this

Seventh Day of November, 2006

JON W. DUDAS
*Director of the United States Patent and Trademark Office*